United States Patent [19]

Finlan et al.

[11] Patent Number: 4,997,278
[45] Date of Patent: Mar. 5, 1991

[54] BIOLOGICAL SENSORS

[75] Inventors: Martin F. Finlan, Aylesbury; John E. M. Midgley; Stephen A. Charles, both of Little Chalfont; James C. Irlam, Staines, all of England

[73] Assignee: Amersham International PLC, Buckinghamshire, England

[21] Appl. No.: 232,650

[22] Filed: Aug. 16, 1988

[30] Foreign Application Priority Data

Aug. 22, 1987 [GB] United Kingdom ................ 8719885
Sep. 4, 1987 [GB] United Kingdom ................ 8720854

[51] Int. Cl.⁵ ..................... G01N 21/41; G01N 21/55; G01J 3/30
[52] U.S. Cl. .................................. 356/128; 356/318; 356/445
[58] Field of Search ............................. 356/127-129, 356/132, 135, 136, 318, 317, 311, 445

[56] References Cited

U.S. PATENT DOCUMENTS

| 2,604,809 | 7/1952 | Mitchell | 250/222.1 |
| 3,650,631 | 3/1972 | Grassel et al. | 356/128 |
| 4,844,613 | 7/1989 | Batchelder et al. | 356/318 |

FOREIGN PATENT DOCUMENTS

| 2222642 | 11/1973 | Fed. Rep. of Germany . | |
| 2173895 | 10/1986 | United Kingdom . | |
| 8705650 | 3/1987 | United Kingdom | 356/445 |

OTHER PUBLICATIONS

"The Air Method With Focused Light—Application to Guided Waves on a Grating", by E. Kretschmann, Optics Communications, vol. 26, No. 1, Jul. 1978, pp. 41-44.
"Surface Plasmon Resonance for Gas Detection and Biosensing", Sensors and Actuators, 4 (1983), pp. 299-304.
Abstract of JP 61-11636-1/1986.
"Infrared Attenuated Total Reflection Spectroscopy at the Metal-Electrolyte Interface", Vacuum/vol. 33, pp. 763-766.
"Optical Nondestructive Method for Dynamic Monitoring of Chemical Reactions", IBM Technical Disclosure Bulletin, vol. 25, No. 10, Mar. 1983.
"Plasmon Surface Polariton Dispersion by Direct Optical Observation", Am. J. Phys., Aug., 1980, pp. 669-672.

Primary Examiner—Richard A. Rosenberger
Assistant Examiner—Hoa Pham
Attorney, Agent, or Firm—Wenderoth, Lind & Ponack

[57] ABSTRACT

A sensor uses the principle of surface plasmon resonance (SPR) to monitor the progress of the reaction between a sample and a sensitive layer (for example an antibody layer). The layer is applied to the rear surface of a metallic film formed on the surface of an optically transmissive component in the form of a hemicylindrical lens and slide. Collimated light from a source is applied via a lens which focuses the incoming beam to a focus at a point to form a fan-shaped spread of light incident at the point. The light is internally reflected at the point, and emerges from the component to be applied to a dectector array which latter is electronically scanned. The angle of incidence of the light at the point is such as to span that angle which gives rise to surface plasmon resonance, together with a range of angles thereabout so that the progress of the resonant condition, as the reaction between the sample and the sensitive layer proceeds, can be monitored.

14 Claims, 3 Drawing Sheets

BIOLOGICAL SENSORS

BACKGROUND OF THE INVENTION

1. Field of the Invention

This invention relates to sensors for use in biological, biochemical and chemical testing and in particular to immunosensors used to monitor the interaction of antibodies with their corresponding antigens.

2. Description of the Related Art

When antibodies are immobilized on a surface, the properties of the surface change when a solution containing a corresponding antigen is brought into contact with the surface to thus allow the antigen to bind with the antibody. In particular, the change in the optical properties of the surface can be monitored with suitable apparatus.

The phenomenon of surface plasmon resonance (SPR) can be used to detect minute changes in the refractive index of the surface as the reaction between the antigen and the antibody proceeds. Surface plasmon resonance is the oscillation of the plasma of free electrons which exists at a metal boundary. These oscillations are affected by the refractive index of the material adjacent the metal surface and it is this that forms the basis of the sensor mechanism. Surface plasmon resonance may be achieved by using the evanescent wave which is generated when a p-polarized light beam is totally internally reflected at the boundary of a medium, e.g. glass, which has a high dielectric constant. A paper describing the technique has been published under the title "Surface plasmon resonance for gas detection and biosensing" by Lieberg, Nylander and Lundstrom in Sensors and Actuators, Vol. 4, page 299. Illustrated in FIG. 1 of the accompanying drawings is a diagram of the eqipment described in this paper. A beam 1 of light is applied from a laser source (not shown) onto an internal surface 2 of a glass body 3. A detector (not shown) monitors the internally reflected beam 4. Applied to the external surface 2 of glass body 3 is a thin film 5 of metal, for example gold or silver, and applied to the film 5 is a further thin film 6 of organic material containing antibodies. A sample 7 containing antigen is brought into contact with the antibody film 6 to thus cause a reaction between the antigen and the antibody. If binding occurs, the refractive index of the layer 6 will change owing to the size of the antibody molecules and this change can be detected and measured using the surface plasmon resonance technique, as will now be explained.

Surface plasmon resonance can be experimentally observed, in the arrangement of FIG. 1, by varying the angle of the incident beam 1 and monitoring the intensity of the internally reflected beam 4. At a certain angle of incidence the parallel component of the light momentum will match with the dispersion for surface plasmons at the opposite surface 8 of the metal film. Provided that the thickness of metal film 5 is chosen correctly, there will be an electromagnetic coupling between the glass/metal interface at surface 2 and the metal/antibody interface at surface 8 as a result of surface plasmon resonance, and thus an attenuation in the reflected beam 4 at that particular angle of incidence. Thus, as the angle of incidence of beam 1 is varied, surface plasmon resonance is observed as a sharp dip in the intensity of the internally reflected beam 4 at a particular angle of incidence. The angle of incidence at which resonance occurs is affected by the refractive index of the material against the metal film 5—i.e. the antibody layer 6—and the angle of incidence corresponding to resonance is thus a direct measure of the state of the reaction between the antibody and their antigen. Increased sensitivity can be obtained by choosing an angle of incidence half way down the reflectance dip curve, where the response is substantially linear, at the beginning of the antibody/antigen reaction, and then maintaining that angle of incidence fixed and observing changes in the intensity of the reflected beam 4 with time.

Known systems of the type described with reference to FIG. 1 utilize a prism as the glass body 3. A diagram showing this arrangement is given in FIG. 2 which is simply an experimental set up intended to demonstrate surface plasmon resonance. The prism is shown under reference 8 and has applied to its undersurface a thin film 5 of metal. Light 1 from a laser source (not shown) is incident on the prism where it is refracted at point 9 before entering the prism. The internally reflected beam 4 is likewise refracted (at point 10) upon exiting from the prism.

One problem with the known SPR systems is the slowness of operation relative to changes in the refractive index of the antibody layer. Another problem, particularly related to the use of the prism shown in FIG. 2, is that, as the angle of incidence is changed, either by moving the source, or rotating the prism, or both, the point on surface 2 at which the incoming beam is incident moves. Because of inevitable variations in the metal film 5 and the coating 6 of antibody, the angle of incidence which results in resonance changes as this movement occurs, which in turn introduces a further variable factor into the measurement and thus makes comparisons between the initial, unbound, state and the bound state of the antibody layer 6 less accurate.

SUMMARY OF THE INVENTION

In the present invention, the speed of response is improved by providing that the incoming beam of radiation which is internally reflected at the glass/metal interface takes the form of a fan-shaped beam of electromagnetic radiation, usually in the visible or near-visible region. In this way, the progress of the resonant condition, as the reaction between the sample and the antibody layer proceeds, can be monitored. In one example, this can be achieved by taking a "solid" input beam from a source of electromagnetic radiation, and bringing it (the beam) to a focus at the point of incidence of the beam on the glass/metal interface. The input beam thus becomes equivalent to several beams incident upon the glass/metal interface over a range of angles. The equipment can be chosen so that the range of angles spans the angle of dip corresponding to surface plasmon resonance together with a range of angles thereabout. The corresponding internally reflected beam is likewise effectively several beams and may be monitored by a large area detector, or by an array of angularly spaced detectors positioned to collect the several emergent beams. Thus the detectors can encode the information from the whole of the dip within milliseconds. In this way, the progress of the resonant condition, as the reaction between the sample and the antibody layer proceeds, can be monitored.

The use of a fan-shaped beam highlights the problems of the prism (see above) and, in order to avoid these, it is provided that the surface of the transparent, usually glass, body onto which the incoming light is incident is a curved, preferably circular, surface and is arranged, with respect to the input beam of electromagnetic radiation, such that the beam enters orthogonally to the tangent to the surface at the point of entry. Preferably likewise, that surface from which the internally reflected beam emerges is a curved, preferably circular, surface.

In a first embodiment of the invention, the transparent body takes the form of a glass hemispherical body whose flat surface is covered with a thin metal film and a sensitive overlayer in the manner described above. The source of input electromagnetic radiation, for example a light source, is arranged so that the input beam enters the hemispherical body orthogonally to the tangent at the point of incidence, and thus the beam passes through unrefracted and is incident at the center of the circular flat surface. The point of incidence on the flat surface is thus the same for all parts of the fan-shaped beam.

Shapes other than hemispherical can be used; for example semicylindrical, which gives a line incidence, rather than a point, or truncated hemispherical or hemicylindrical in which the top is cut off—i.e. to form a body having two flat, probably parallel, surfaces with arcuate sides joining the surfaces.

The fan-shaped beam may be constrained to be substantially planar by being projected through a slit lying in a plane passing through the point of incidence and oriented vertically to that of the glass/metal interface. Alternatively, the expression "fan-shaped" may refer to a shape of a section of the input beam, and the beam itself may extend in other planes—for example wedge-shaped (giving a line of incidence), or conical shaped.

Although the layer applied to the metal film is described herein as an antibody layer for use in immunoassays, it will be seen that any sensitive layer whose refractive index changes upon an event occurring can be used to thus provide a sensitive detector having a wide variety of applications in the fields of biology, biochemistry and chemistry. As an example, the sensitive layer could be a DNA or RNA probe which would, during the test, bind with its complement in solution as represented by the sample to be tested.

The metal film material is commonly silver or gold, usually applied by evaporation. The film needs to be as uniform as possible in order to cater for minute movement in the point of incidence of the incoming beam. It is assumed that a structured metal film will give the best resonance and there are various ways in which the glass body can be pretreated to improve the performance of the metal film and in particular to control the natural tendency of such films to form discontinuous islands:

1. Immersion in molten metal nitrates and other molten salts. This has the effect of introducing ions into the surface in a manner which can be structured and which can act as foci for island formation.

2. Ion bombardment of cold or hot glass to introduce nucleating sites. The removal of the more mobile ions has been demonstrated to reduce the thickness at which the evaporated film becomes continuous.

3. Electroless plating or electroplating over lightly evaporated films (0 to 100 angstroms thick). Electroless plated films survive to a greater thickness than evaporated films and could form more stable nuclei for subsequent coating.

4. Evaporation on to electroless plated films. The electroless plated films have a stronger tendency to an island structure and to bigger islands with greater spacing than evaporating films. This could be of advantage in tuning to light of a prescribed wavelength.

Coating performance can also be improved by:

1. Controlling the glass surface temperature during coating. Using a higher temperature substrate increases the islands' size and the spacing between them and conversely.

2. Evaporating in the presence of a magnetic or electrostatic field or electron emission device to control the ion content of the vapor stream. The state of charge of the substrate is know to affect the island structure.

3. Controlling the angle of incidence of the evaporated vapor stream relative to the glass surface. The mobility of the evaporated atoms and hence their ability to form bigger islands is greater when the momentum of the atoms relative to the glass surface is increased.

BRIEF DESCRIPTION OF THE DRAWINGS

In order that the invention may be better understood, some embodiments thereof will now be described by way of example only and with reference to the accompanying drawings in which.

DETAILED DESCRIPTION OF THE PREFERRED EMBODIMENTS

Figure 1:
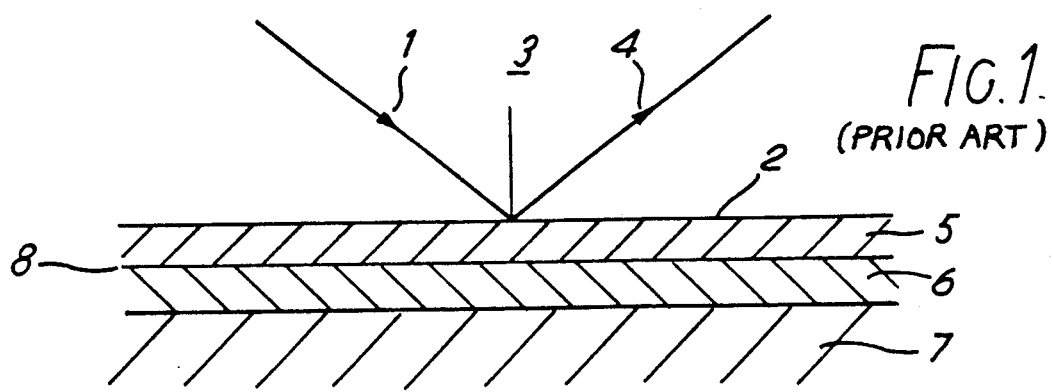
FIGS. 1 and 2 are diagrams of known experimental arrangements for demonstrating the surface plasmon resonance effect.
Figure 2:
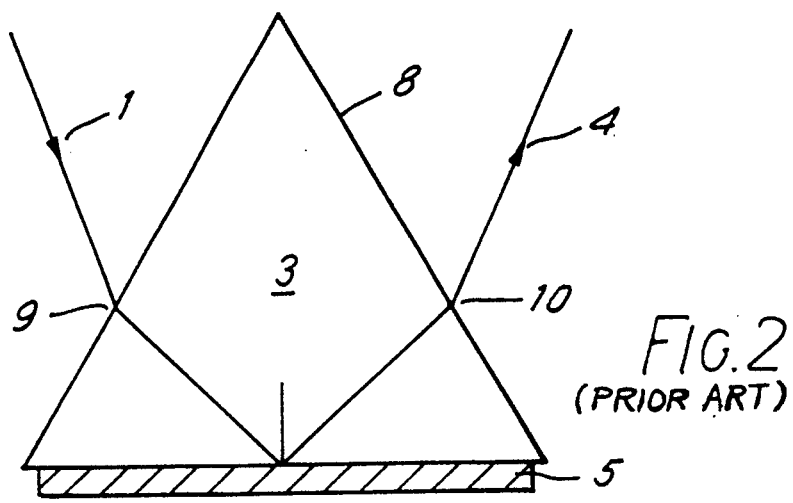
Figure 3:
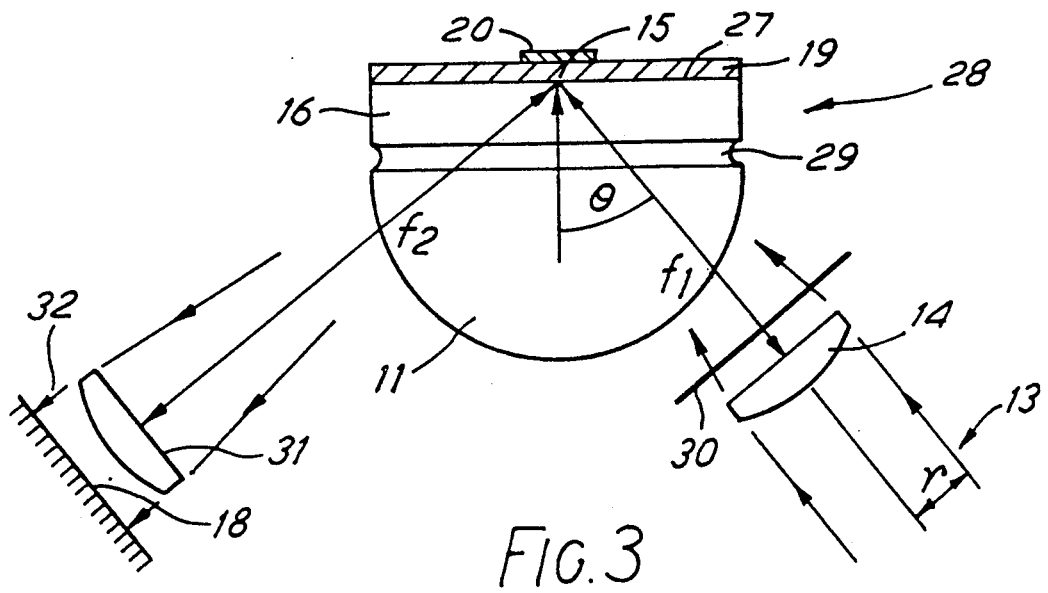
FIG. 3 shows, in schematic outline, a cross-sectional view of a sensor in accordance with one example of the invention.

Referring now to FIG. 3, a collimated beam 13 of electromagnetic radiation of width 2 r from a source, which is not shown but may conveniently comprise a laser diode collimator pen such as that manufactured under the model number TXCK 1200 by Telefunken Electronic, is incident upon a hemi-cylindrical focussing lens 14 of focal length $f_1$, which causes the light to converge to a point 15 on an interface 27 between an optically transmissive component, generally shown at 28, and a reflective layer 19 in the form of a metallic coating. The optical component is, in this example, made up of a glass support plate or slide 16 having a first surface (upon which the reflective layer is coated,) and a hemispherical lens 11 having a second, curved, spherical surface with its center of curvature located at the point 15. A suitable index matching fluid is provided, as shown at 29, between the facing surfaces of plate 16 and lens 11 and the arrangement is such that all light rays in the convergent beam which emerges from lens 14 travel radially of the optically transmissive component 28 and thus undergo no refraction and are focussed centrally on the point 15. A slit 30 constrains the convergent beam to a substantial planar fan shape, so that only a small area of reflective layer 19 is illuminated to reduce any effects due to non-uniformity of the metal coating.

The light internally reflected from point 15 travels as a divergent, planar, fan-shaped beam back out of the component 28, through a third surface thereof contiguous to the second surface as shown in FIG. 3, and is incident upon a focussing lens 31 which transmits such light as a light beam 32 which is substantially parallel-sided, or at least of reduced divergence compared to the fan-shaped beam of light emergent from component 28. Beam 32 is arranged to be incident upon a detector 18, for example an array of photo-sensitive detectors, and in particular an angular array, and it will be appreciated that the main purpose of lens 31 is to reduce stray reflections in the array 18 ensuring that beam 32 is normal to its surface. If, however, the stray reflections are not of significance or if the array 18 can be conveniently placed close to the exit surface of component 28 (possibly even attached to or deposited on that surface) lens 31 is not required.

The array of detectors is arranged to generate electrical signals indicative of the variation of intensity of light with position across the beam 32; the SPR effect dictating that strong absorption will occur at a particular angle as determined by material in the fluid to which the reflective layer 19 is exposed. These electrical signals are sampled and digitized and fed to a suitable analyzing arrangement which may include a microprocessor or larger computer.

It can be desirable, in the interests of minimizing the disturbing effects of extraneous light without having to resort to the expense and inconvenience of shrouding the entire arrangement, or at least the components 5 and 28, to arrange that a characteristic modulation is impressed upon the light and that the detectors and/or the processing circuits are "tuned" to respond preferentially to such modulation.

Figure 4:
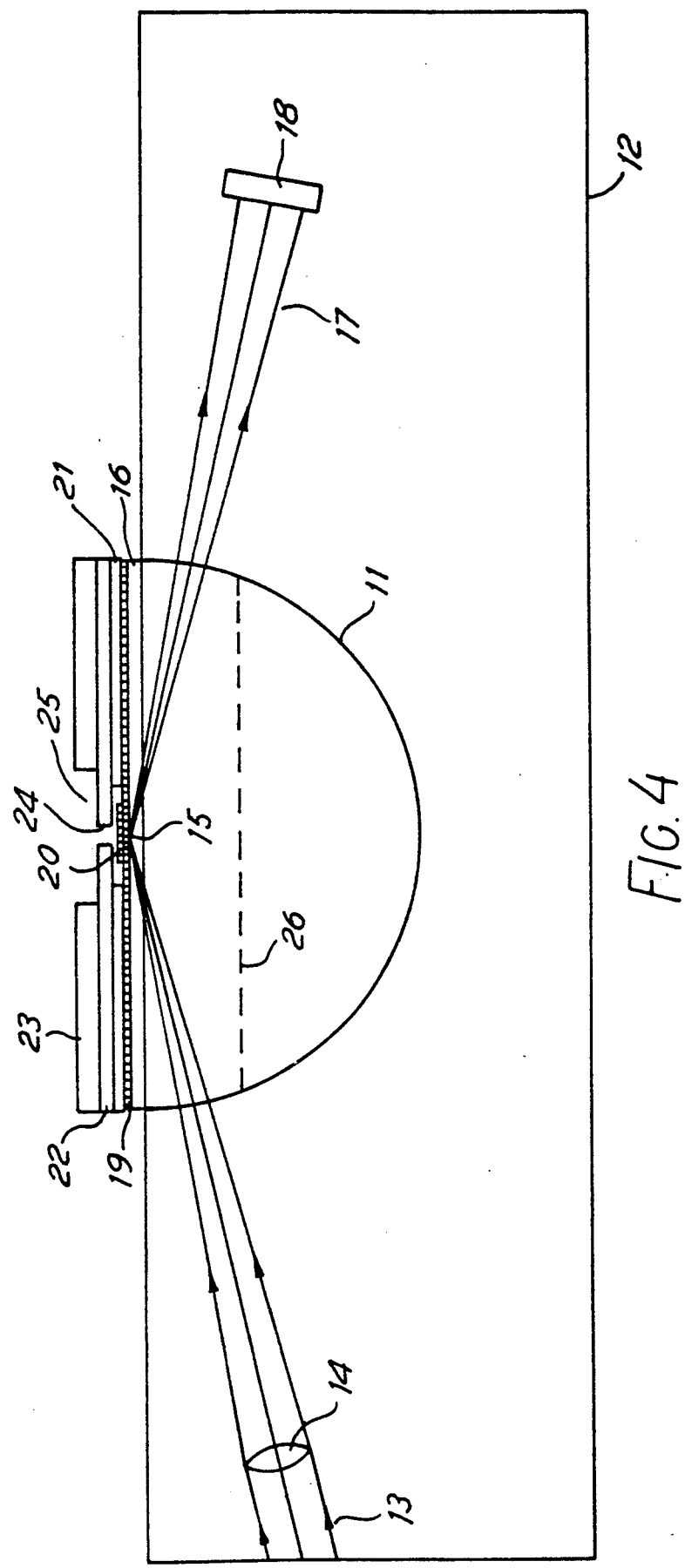
FIG. 4 is a diagrammatic side view of another example of a sensor according to the present invention.

A second embodiment of the invention will now be described by reference to FIG. 4. Referring to FIG. 4, the apparatus comprises a hemispherical body 11 made of transparent material such as glass or quartz housed within a casing 12. A source (not shown) of electromagnetic radiation produces a collimated input beam 13 of electromagnetic radiation. The frequency of the radiation must be such as to result in the generation of surface plasmon waves and in practice will be within or near the visible region. Suitable sources include a helium neon laser or an infrared diode laser, but an ordinary light source, with suitable filters and collimators, could be used.

A lens 14 is used to bring the parallel input beam 13 to a focus at a point 15 spaced just above the center of the circular flat surface of the hemispherical body 11. The point 15 lies on the surface first surface of a slide 16 made of transparent material such as glass whose refractive index is equal or close to that of the hemispherical body 11. The arrangement is such that the point 15 lies at the approximate center of curvature of the curved spherical, surface second surface of the hemispherical body.

Radiation which is internally reflected at point 15 passes, through a third surface contiguous to said second surface, out of the hemispherical body in the form of a divergent beam 17 and passes into a radiation sensitive detector 18 which gives an electrical output signal for analysis by external circuitry (not shown) in the manner described above. The detector may, for example, be a diode array, or a charge couple device or similar imaging device.

In a practical realization of the apparatus, the metal film layer, shown under reference 19, is applied to the surface of the aforementioned slide 16. The point 15 to which the input beam is focussed thus lies on the interface between the metal film and the slide 16. Applied to the surface of the metal film is a sensitive layer 20 whose refractive index changes as the test progresses. The sensitive layer may, for example, be an antibody layer.

The sensitive layer 20 is restricted to a relatively small active zone about the point 15 and within a central hole provided in a circular disc 21 of absorbent material. Overlying disc 21 are two further discs 22, 23 of non-absorbent material. A central aperture in upper disc 23 defines a well 25 into which a sample to be tested is placed. A central aperture 24 in disc 22 is of a size to cause liquid in well 25 to travel by capillary action into the active zone above layer 20. The thickness of disc 21 is such as to define a depth for the active zone such as to promote radially outward movement of the sample liquid emerging from aperture 24 by capillary action. The absorbent disc 21 absorbs sample which has flowed past the active zone.

The whole unit comprising slide 16, disc 21 and discs 22 and 23 is disposable so that a fresh unit, including sensitive layer 20 can be used for each test. The slide 16 is placed upon the flat surface of the hemispherical body 11, preferably after applying to the flat surface a thin layer of optical oil or grease to ensure good optical coupling between the hemispherical body and the slide. Optionally, the hemispherical body itself may be disposable, provided it can be produced cheaply enough, in which case there would be no need to include a separate slide 16, and the metal film 19 can be applied direct to the hemispherical body.

In order to use the apparatus, a sample to be tested, and containing an antigen capable of binding with the antibody molecules in layer 20, is placed in the well 25 and passes through aperture 24 by capillary action. Emerging from aperture 24, the liquid sample commences to flow radially outwards in all directions towards the absorbent disc 21, passing as it does so the antibody layer 20. The sample adjacent the layer 20 is thus being constantly replenished during the course of the test, which ensures maximum sensitivity.

As the sample flows past the layer 20 any antigen within the sample capable of binding with the antibody in layer 20 will do so, thus altering the refractive index of layer 20 as the reaction proceeds. This change in refractive index is continuously monitored during the test by directing at the point 15 the focussed light beam 13. Provided that conditions are correct—in particular the angle of incidence at the point 15 is correct—the application of beam 13 will result in the generation of a plasmon wave, thus extracting energy from the input beam and causing an attenuation in the intensity of the output beam 17 at a particular angle of incidence. The input beam is arranged such that the mid-angle of the range of angles of the input beam is approximately halfway down the reflectance dip, as described above, and the test is carried out at a constant angle of incidence, monitoring the intensity of the reflected beam above and below this mid point level. This gives a linear and highly sensitive output.

The initial reflectance dip which is chosen for setting up the angle of incidence should be the dip which results when some neutral or buffer solution is passed through the cell, or when the sample under test is passed through the cell but before any reaction thereof has taken place. In connection with the latter method, which is currently preferred, it is to be noted that, as sample begins to flow past the active zone adjacent layer 20 the refractive index does not start to change immediately due to the antibody/antigen reaction. There is thus sufficient time to take an initial reading with the unreacted sample flowing past, which reading can be utilized, using feedback circuitry to rapidly adjust the angle of incidence to an appropriate value halfway down the reflectance dip, so that the rest of the test can be performed at this fixed angle.

In an embodiment of the invention, the hemispherical body 11 is replaced by a semicylindrical body. In this case FIGS. 3 and 4 can be regarded as sections through a suitable apparatus, with the semicylindrical body 11 extending above and below the paper. The use of a semicylindrical body gives the possibility of a line area of resonance instead of the single point 15, and hence a linear active zone. The aperture 24 becomes a slit, and the well 25 becomes elongate. The light source is operable to generate a "sheet" output beam which may be focused by a cylindrical lens of the type shown in FIG. 3 by reference numeral 31 onto a line extending through point 15. The detector 18 is likewise linear in extent and is preferably composed of separate detectors or detector arrays, each arranged to monitor a specific section along the length of the line 15.

The semicylindrical lens 11 has the advantage that it can be used to perform several tests simultaneously on a single sample. To this end, the layer 20 takes the form of a series of distinct sensitive areas, each comprising a different antibody, with each separate area being monitored by its own detector 18. A single sample introduced into well 25 will flow through the slot 24 into the active area and will react simultaneously with the various sensitive areas, giving individual output readings which can be monitored at detectors 18.

Although the hemispherical/semicylindrical body 11 is shown as having a complete 180° curvature, in fact it will be noted that only that part near the flat surface is used and therefore a substantial portion of the body 11 can be cut away to form a truncated hemispherical or semicylindrical body, as indicated, by way of example, by the dotted line 26 in FIG. 4.

As will be appreciated from the foregoing, the invention enables a whole, or at least a significant part of, the spread of angles of interest to be investigated at once; the speed of investigation being limited only by the response characteristics of the detectors in the array 18 and of the associated sampling and computing circuits. This enables initial transients and other shifts which may occur during the analysis to be monitored and allowed for and also permits rapid calibratory checks to be made. Furthermore it has been found that, if each analysis, or assay, is started at a fixed value of reflectivity (as determined by a suitable output from the computing circuits) then the absolute refractive index of the fluid sample, which may well vary between samples, is unimportant. Importantly, the invention enables the desired reflectivity characteristic to be determined on a time scale so short that it is less than the time taken for the chemical bonding, necessary to SPR, to be achieved between the relevant constituent of the fluid sample and the reflective layer.

A further advantage of the invention is that it permits calibratory scans to be conducted with fluids of known SPR characteristics to generate compensating data which can be held in the computing circuits, and automatically applied as corrections if desired during clinical analysis. This compensating data can be used, for example, to allow for variations in reflectivity over the point 15, a phenomenon which can occur particularly if the reflective layer is produced by evaporation.

Figure 5A:
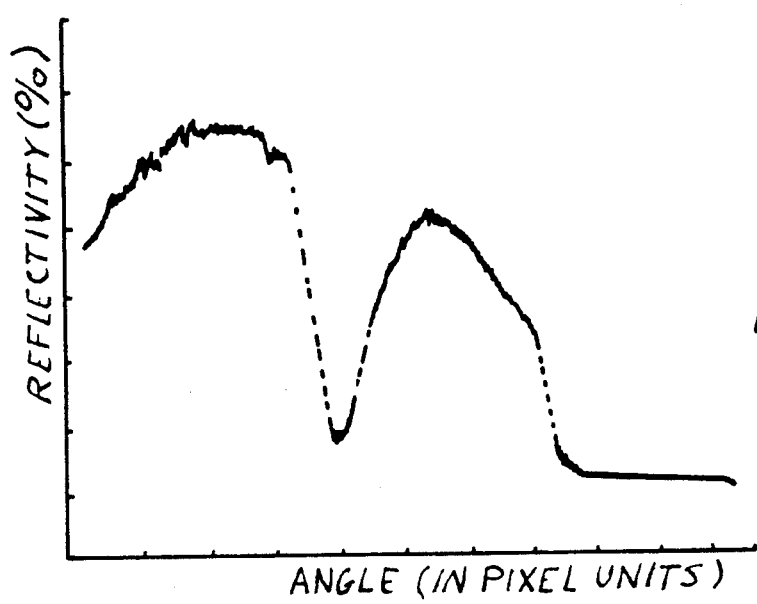
FIGS. 5(a) and 5(b) illustrate the performance of which an arrangement in accordance with the invention is capable.

FIG. 5 shows a representation of a video signal derived from the detector 18 in the arrangement of FIGS. 3 and 4, as displayed on an oscilloscope screen. The SPR resonance can be clearly seen.

Figure 5B:
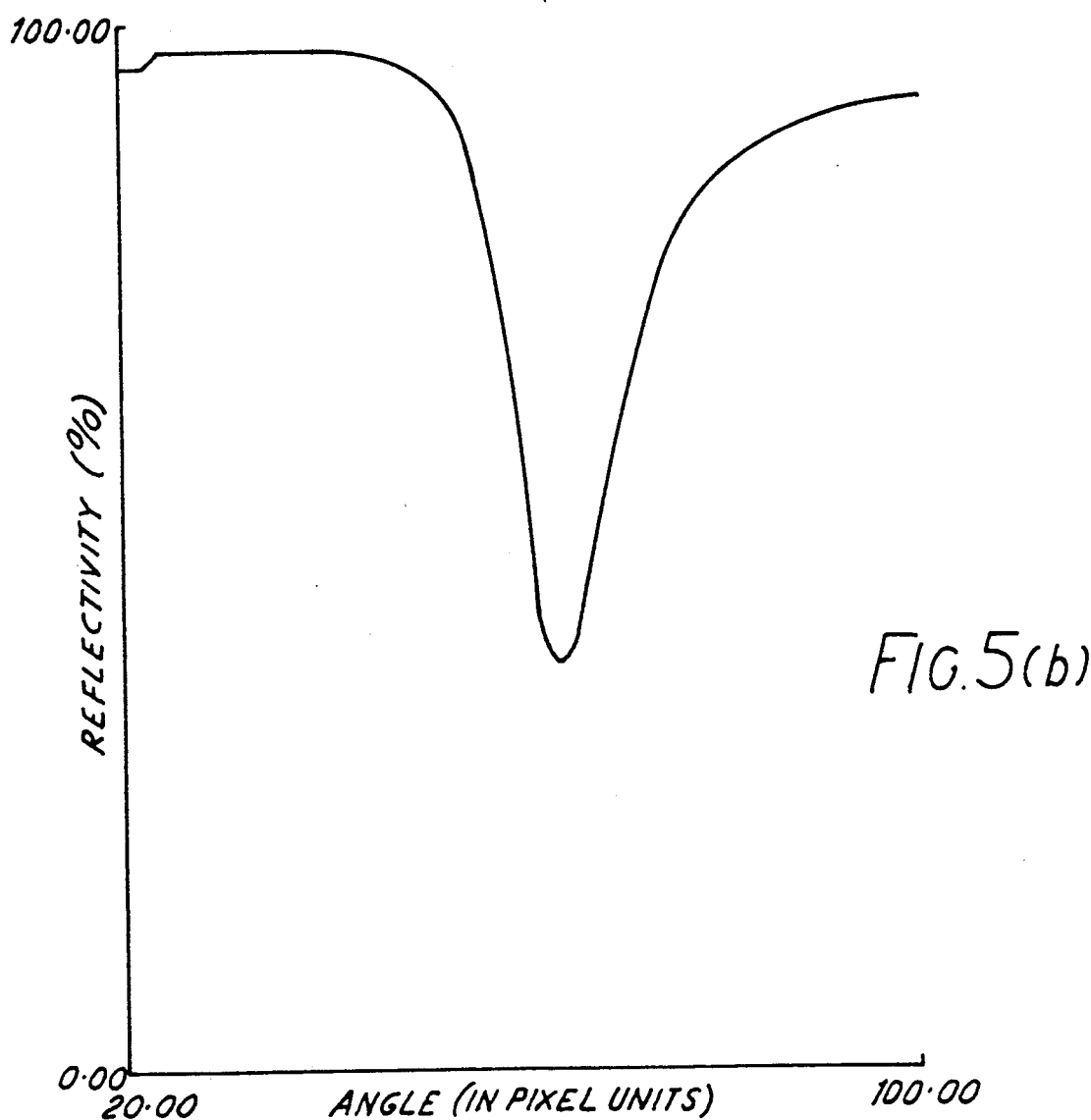

The detector is electronically scanned, typically at approximately 200 times per second, to allow the movement of the resonance to be viewed in "real-time" as biochemicals are bound to the surface of the metal coated plate 16. The reflectivity curve in FIG. 5a has been modulated by the approximately Gaussian profile of the beam from the laser diode source. This profile can be removed by appropriate signal processing as shown in FIG. 5b, which was produced by subtraction of the fixed backround due to ambient light and division by the signal without any resonance.

We claim:

1. A sensor for use in biological, biochemical or chemical testing, said sensor comprising a block of material transparent to electromagnetic radiation, a layer of metallic material applied to at least part of a first surface of said block, a layer of sensitive material applied to the metallic layer, means for introducing onto the sensitive layer so as to react therewith a sample to be analyzed, a source of electromagnetic radiation, said radiation being directed into said transparent block in such a way as to be internally reflected off said part of said surface, means for converging said radiation onto said part of said surface in such a way that the incoming beam is a convergent fan-shaped beam and spans a range of angles of incidence including that which causes surface plasmon resonance to occur, the characteristics of which resonance are dependent upon the reaction between the sample and the sensitive layer, and detector means positioned to receive the internally reflected beam for detecting the characteristics of the resonance that are dependent upon the reaction between the sample and the sensitive layer.

2. A sensor as claimed in claim 1 wherein the radiation from said source enters the block through a second, curved, surface.

3. A sensor as claimed in claim 2 wherein the center of curvature of said second, curved, surface lies on said first surface.

4. A sensor as claimed in claim 2 wherein said second surface is spherical.

5. A sensor as claimed in claim 2 wherein the input beam of electromagnetic radiation enters the block in a direction orthogonal to a tangent to the second, curved, surface at the point of entry.

6. A sensor as claimed in claim 2 wherein said detector means is positioned externally of said block, and wherein the internally reflected beam emerges from said block through a third surface of the block, said third surface being curved.

7. A sensor as claimed in claim 6 wherein the center of curvature of said third surface lies on said first surface.

8. A sensor as claimed in claim 2 wherein said transparent block takes the form of a hemisphere whose flat surface is said first surface and whose spherical surface includes said second surface, and wherein said part of said first surface is positioned at the center of the first surface.

9. A sensor as claimed in claim 2 wherein said transparent block takes the form of a semicylinder whose flat surface is said first surface and whose curved surface includes said second surface and wherein said part of said first surface is positioned on the longitudinal central axis of said first surface.

10. A sensor as claimed in claim 2 wherein said transparent block takes the form of a truncated hemisphere one of whose flat surfaces is said first surface and whose spherical surface includes said second surface, and wherein said part of said first surface is positioned at the center of the first surface.

11. A sensor as claimed in claim 2 wherein said transparent block takes the form of a truncated semicylinder one of whose flat surfaces is said first surface and whose curved surface includes said second surface, and wherein part of said first surface is positioned on the longitudinal central axis of said first surface.

12. A sensor as claimed in claim 1 wherein the detector means takes the form of a large-area detector positioned to collect the whole emergent beam.

13. A sensor as claimed in claim 1 wherein the detector means takes the form of an array of angularly spaced detectors positioned to collect the whole emergent beam.

14. A sensor as claimed in claim 1 wherein said sensitive layer takes the form of an antibody layer to be reacted with a sample containing a corresponding antigen.

* * * * *